US006355041B1

(12) United States Patent
Martin

(10) Patent No.: US 6,355,041 B1
(45) Date of Patent: Mar. 12, 2002

(54) BONE PIN-PLATE SURGICAL DEVICE AND METHOD FOR PROMOTING ATHRODESIS OF THE EQUINE FETLOCK JOINT

(75) Inventor: George S. Martin, New Roads, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/772,784

(22) Filed: Jan. 30, 2001

(51) Int. Cl.[7] .............................................. A61B 17/72
(52) U.S. Cl. .............................. 606/62; 606/60; 606/69
(58) Field of Search ............................. 606/62, 64, 69, 606/60

(56) References Cited

U.S. PATENT DOCUMENTS 4,773,416 A * 9/1988 Hourahane
4,794,919 A * 1/1989 Nilsson
5,603,715 A * 2/1997 Kessler ........................ 606/63

FOREIGN PATENT DOCUMENTS

EP            561295 A1 * 9/1993 .................. 606/62

OTHER PUBLICATIONS

Bramlage, L., "An Initial Report on a Surgical Technique for Arthrodesis of the Metacarpophalangeal Joint in the Horse," Proceedings of the American Association of Equine Practitioners, vol. 27, pp. 257–261 (1982).
Bramlage, L., "Arthrodesis of the Metacarpophalangeal Joint —Results in 43 Horses, (Abstract)" Veterinary Surgery , vol. 14, p. 49 (1985).
Bramlage, L., "Fetlock Arthrodesis." in: Nixon, A.J., Equine Fracture Repair , (Pennsylvania, W.B. Saunders Company, 1996), pp. 172–178.
Crawley, G. et al., "A Modified Cloward's Technique For Arthrodesis of the Normal Metacarpophalangeal Joint in the Horse," Veterinary Surgery , vol. 17, pp. 117–127 (1988).
Herthel, D., "Application of the Interlocking Intramedullary Nail." in: Nixon, A.J., Equine Fracture Repair, (Pennsylvania, W.B. Saunders Company, 1996), pp. 371–376.
Kainer, R., "Functional Anatomy of Equine Locomotor Organs." in: Stashak, T.S., Adams'Lameness in Horses (Philadelphia, Lea & Febiger, 1987), pp. 10–18.
Les, C.M. et al., "Ex Vivo Simulation of In Vivo strain Distributions in the Equine Metacarpus," Equine Vet J, vol. 30, pp. 260–266 (1998).
McDuffee, L. et al., "Limb Loading Activity of Adult Horses Confined to Box Stalls in an Equine Hospital Barn," American Journal of Veterinary Research, vol. 61, pp. 234–237 (2000).
Muller, M. et al., Manual of Internal Fixation: Techniques Recommended by the AO Group, ($2^{nd}$ ed., Springer–Verlag, 1979) pp. 42, 58.
Richardson, D. et al., "Use of an External Skeletal Fixation Device and Bone Graft For Arthrodesis of the Metacarpophalangeal Joint in Horses," Journal of the American Veterinary Medical Association, vol. 191, pp. 316–321 (1987).
Valdez, H. et al., "Arthrodesis of the Fetlock Joint With Dynamic Compression Plates," Journal of Equine Medicine and Surgery, vol. 3, pp. 421–427 (1979).

* cited by examiner

Primary Examiner—Jeffrey A. Smith
(74) Attorney, Agent, or Firm—John H. Runnels; Andre J. Porter

(57) ABSTRACT

A device and surgical method for promoting arthrodesis of an equine fetlock joint. The device is a rigid bone pin-plate that is implanted at the fetlock joint and attached to the tension band surface of the first phalanx. The surgical method is a palmar surgical approach for implanting a bone pin-plate device that provides access to the medullary canal of the third metacarpal bone.

17 Claims, 6 Drawing Sheets

BONE PIN-PLATE SURGICAL DEVICE AND METHOD FOR PROMOTING ATHRODESIS OF THE EQUINE FETLOCK JOINT

This invention pertains to a surgical implant and method to stabilize equine fetlock joints with a bone pin-plate that inserts into the third metacarpal bone and attaches to the tension surface of the first phalanx.

Horses, like humans, are susceptible to injuries sustained through physical exercise. The most common injuries sustained by horses are bone and joint fractures. While horses are usually capable of a complete recovery from minor bone fractures, a breakdown fracture in the ankle area, referred to as the fetlock joint or metacarpophalangeal joint, is usually catastrophic. Breakdown fractures can occur when the supporting structures of the fetlock joint give way under stress. Without the use of this supporting structure, a horse cannot satisfactorily support its own body weight.

Horses with catastrophic injuries to the fetlock supporting structure usually do not have an athletic future. Therefore, the goal of treatment is usually to salvage a horse for breeding by stabilizing the fetlock joint through arthrodesis. "Arthrodesis" is the surgically-induced fusion of the bones of a joint. Complications often follow arthrodesis, including support limb laminitis, infection, implant failure, and cast sores. Such complications often mean that the treatment is ultimately unsuccessful.

The angles of the fetlock joint and the position of surrounding soft tissue make surgical stabilization of the fetlock supporting structure difficult. Surgical fixation with a bone plate is a method used for stabilization. However, the bone plate usually experiences fatigue failure due to cycling when placed on the compression side (dorsal side) of the third metacarpal bone, because the plate acts as the load carrying member. See M. Muller et al., *Manual of Internal Fixation: Techniques Recommended by the AO Group,* ($2^{nd}$ ed., Springer-Verlag, 1979) pp. 42, 58. As illustrated in FIG. 2, the compression side 28 of the third metacarpal bone is the side that experiences compression when weight is applied to the fetlock joint.

Unfortunately, the tension band side (palmar surface) of the horse's fetlock joint lies beneath important supporting soft tissues. As illustrated in FIG. 2, the tension band side 26 of the fetlock joint 10 is the side that experiences expansion as weight is applied to the fetlock joint 10. See R. Kainer, "Functional Anatomy of Equine Locomotor Organs." in: Stashak, T.S., *Adams' Lameness in Horses* (Philadelphia, Lea & Febiger, 1987), pp. 10–18. Equine surgeons have generally considered surgical approaches through these soft tissue structures too risky. Rather than risk damage to the soft tissues, surgeons have avoided the tension band side by placing the bone plate on the compression surface because the dorsal side is easier to access.

To minimize cyclic fatigue of the bone plate, most surgeons arthrodese (fuse) the fetlock joint into an unnatural straight line, resulting in an extended limb length. Horses usually adapt to the fusing of their fetlock joints in this unnatural position. However, unnatural fusion of the joints often causes a horse to overload its pastern and coffin joints because of uneven leg lengths, eventually causing secondary degenerative joint disease and pastern joint subluxation. See L. Bramlage, "An Initial Report on a Surgical Technique for Arthrodesis of the Metacarpophalangeal Joint in the Horse," *Proceedings of the American Association of Equine Practitioners,* vol. 27, pp. 257–261 (1982); and G. Crawley et al., "A Modified Cloward's Technique For Arthrodesis of the Normal Metacarpophalangeal Joint in the Horse," *Veterinary Surgery,* vol. 17, pp. 117–127 (1988).

Currently, there are four fundamentally different surgical devices to arthrodese horses' fetlock joints. FIG. 1 illustrates a front plan view of one embodiment of an external skeletal fixation device. The device comprises transfixation pins 2, an external frame having a foot plate 4, and ascending vertical bars 6 placed on both sides of the third metacarpal bone 14. The transfixation pins 2 are inserted through the third metacarpal bone 14 and attached to the vertical bars 6. The foot plate 4 is attached to the hoof 8. However, this external fixation device is prone to infections and stress concentration around the pin-bone interfaces. See D. Richardson et al., "Use of an External Skeletal Fixation Device and Bone Graft For Arthrodesis of the Metacarpophalangeal Joint in Horses," *Journal of the American Veterinary Medical Association,* vol. 191, pp. 316–321 (1987).

FIG. 2 illustrates a perspective view of one embodiment of a modified Cloward device. Two holes are drilled through the fetlock joint 10 and a steel basket 12, packed with autogenous porous bone, is driven into each hole. However, the stainless steel baskets 12 can induce stresses and have caused fractures emanating from the baskets into the proximal phalanx and the third metacarpal bone. See Crawley et al., 1988.

FIG. 3 illustrates a perspective view of one embodiment of an interlocking intramedullary nail device. A hole is drilled through the third carpal bone (not shown) into the medullary canal of the third metacarpal bone 14 and the first phalanx 16. An interlocking nail 18 is inserted through the third carpal bone, the metacarpal bone 14, and the first phalanx 16. Screws 20 are inserted through the interlocking nail 18, along the longitudinal axis of the first phalanx 16 and the metacarpal bone 14. See D. Herthel, "Application of the Interlocking Intramedullary Nail." in: Nixon, A. J., *Equine Fracture Repair,* (Pennsylvania, W. B. Saunders Company, 1996), pp. 371–376. However, clinical experience has shown that the interlocking nail method requires the fetlock joint be placed in an unnatural, completely straight position.

The most commonly used device today is the plate and tension-band wire device. FIG. 4 illustrates a side plan view of one embodiment of a plate and tension-band wire device. A plate 22 having one end contoured to fit the top surface of the first phalanx 16 is attached to the first phalanx 16 using screws 20, while the second end extends along the longitudinal axis of the third metacarpal bone 14. A figure eight tension-band wire 24 is placed on the tension surface through holes drilled transversely through the first phalanx 16 and third metacarpus 14 to absorb some of the cyclic load. After tightening the tension-band wire 24, screws 20 are inserted through the plate 22 and into the third metacarpal bone 14 to secure the fetlock joint 10. See H. Valdez et al., "Arthrodesis of the Fetlock Joint With Dynamic Compression Plates," *Journal of Equine Medicine and Surgery,* vol.3, pp. 421–427 (1979); and L. Bramlage, "Fetlock Arthrodesis." in: Nixon, A. J., *Equine Fracture Repair,* (Pennsylvania, W.B. Saunders Company, 1996), pp. 172–178. Nevertheless, a significant number of patients must be euthanatized (19 out of 43 cases in one study), usually because of support limb laminitis. See L. Bramlage, "Arthrodesis of the Metacarpophalangeal Joint—Results in 43 Horses,(Abstract)" *Veterinary Surgery,* vol. 14, p. 49 (1985).

Support limb laminitis results from persistent, severe lameness arising from the inability of a horse to support all of its body weight on one leg. Asymmetric limb loading causes mechanical failure of the attachments between the hoof and the bone in the hoof. Horses treated with the tension-band wire technique will likely remain lame because the fixation is not optimally stable. Unstable fixations result in movement between the bone ends, causing pain, slower healing, and prolonged unilateral weight bearing. See Muller et al., 1979. All of these factors increase the probability of support limb laminitis.

I have discovered a bone pin-plate and a surgical method that promote bone fusion of a fetlock joint breakdown by supporting and stabilizing the limb. The device is a bone pin-plate combination capable of being implanted and attached to the tension band surface (rear surface) of the first phalanx. The device comprises a proximal end having a cylindrically-shaped pin, and a distal end having a plate extending at an angle away from the longitudinal axis of the pin. The cylindrically-shaped pin is adapted to be inserted through the center of the third metacarpal bone. The pin merges with a plate upon exiting the third metacarpal bone, preferably as an integral piece.

The bone pin-plate incurs a tension force when weight is applied to the fetlock joint, whereas prior devices incur a compression force, which tends to cause cycling, eventually resulting in mechanical failure. The bone pin-plate's rigid construction substantially eliminates cycling. The bone pin-plate is inserted through the center of the third metacarpal bone, and thus evenly distributes weight along the length of the bone. Additionally, the bone pin-plate allows a surgeon to support and stabilize a fractured fetlock joint in a natural position.

The invention allows the relatively inexpensive, stable fixation of an equine fetlock joint after a fetlock joint fracture, through the tension band surface of the first phalanx. Because the novel bone pin-plate uses the tension band surface of the first phalanx, it reduces mechanical failure, unilateral weight bearing, and pain. Thus, the bone pin-plate promotes an increased healing rate of an equine fetlock fracture.

BRIEF DESCRIPTION OF THE DRAWINGS

FIGS. 5 and 6 illustrate an embodiment of the novel bone pin-plate device 29. FIG. 5 illustrates a perspective view of the device. This embodiment comprises a proximal end 30 having a rigid, cylindrically-shaped pin 32, and a distal end 34 having a rigid, rectangular-shaped plate 36 extending at an angle between approximately 105° and 175°, preferably about 135° from the longitudinal axis of the pin 32. Optionally, at least one screw maybe inserted, using an insert guide, into one or more perpendicular holes 38 drilled through the pin 32 to prevent or reduce torsional movement of the pin 32 after implantation. The bone pin-plate device 29 maybe made of stainless steel, titanium, or a material that promotes bone growth, such as a carbon fiber material. In a preferred embodiment, the rectangular-shaped plate 36 has at least four drill hole 40 spaced evenly along the center of its longitudinal axis.

FIG. 6 illustrates a side plan view of one embodiment of the bone pin-plate 29 inserted into the medullary canal 38. In this embodiment, the cylindrically-shaped pin 32 is sized to be inserted into the medullary canal 38 of the third metacarpal bone 14 to a position below the carpometacarpal joint (not shown), and to support the weight applied to the equine fetlock joint 10. A hole having dimensions that complement the length and diameter of the rigid, cylindrically-shaped pin 32 is drilled into the medullary canal 38.

As shown in FIG. 6, the angle created between the cylindrically-shaped pin 32 and the rectangular-shaped plate 36 allows the fetlock joint 10 to be affixed to the rectangular-shaped plate 36 in a natural position. The dimensions and shape of the contact surface of the rectangular-shaped plate 36 complement the contact surface of the first phalanx 16, such that when the rectangular-shaped plate 36 is attached to the first phalanx 16, there will exist little, if any cycling as weight is periodically applied to the fetlock joint 10. The first phalanx 16 is attached to the rectangular-shaped plate 36 by inserting screws 20 that have a high pull out strength, such as cortical bone screws (Synthes Ltd., Paoli, Pennsylvania), through drill holes, to a depth within the first phalanx 16 sufficient to prevent the screws 20 from being pulled out when weight is applied to the fetlock joint 10.

Figure 1:
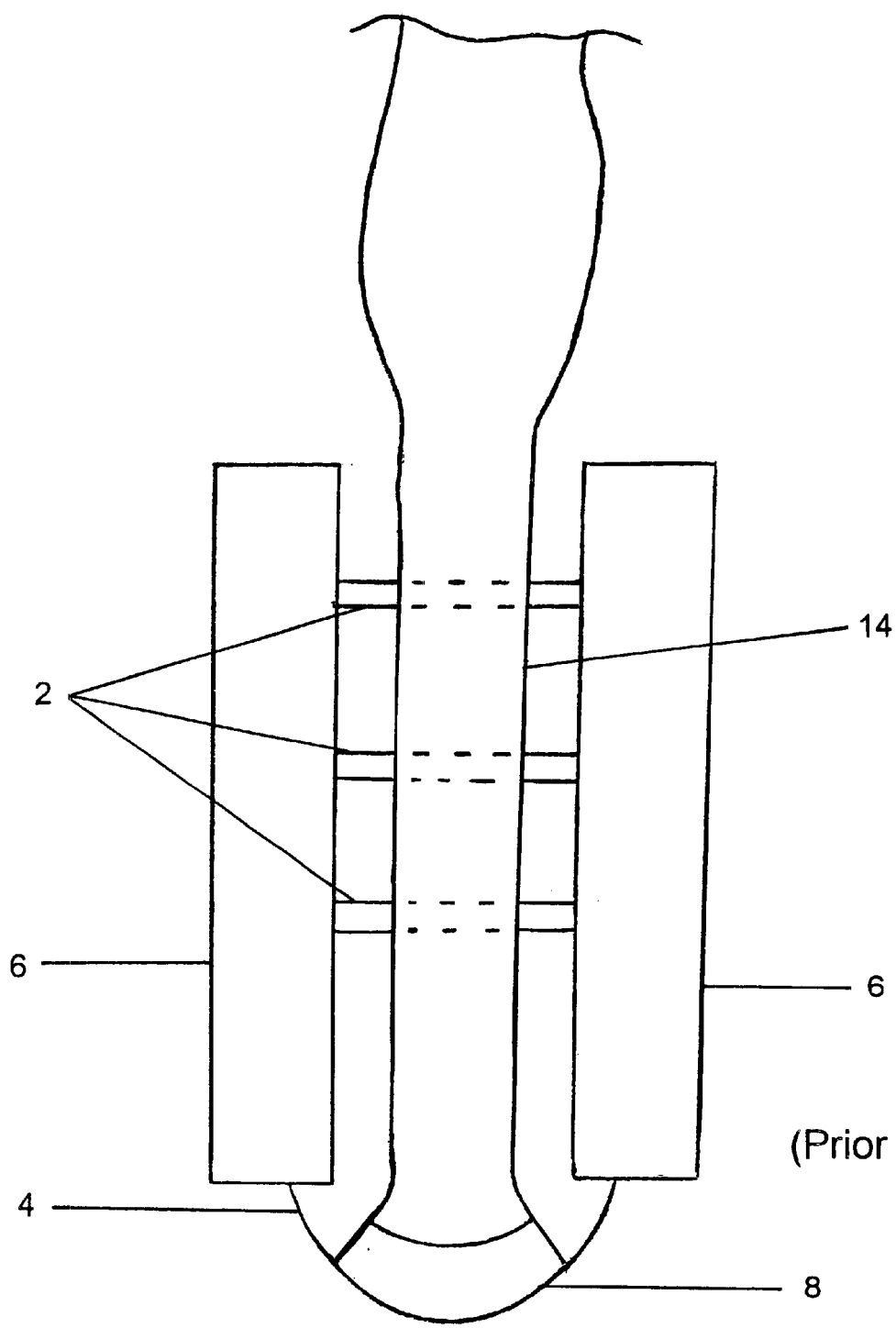
FIG. 1 illustrates a front plan view of one embodiment of a prior art external skeletal fixation device.
Figure 2:
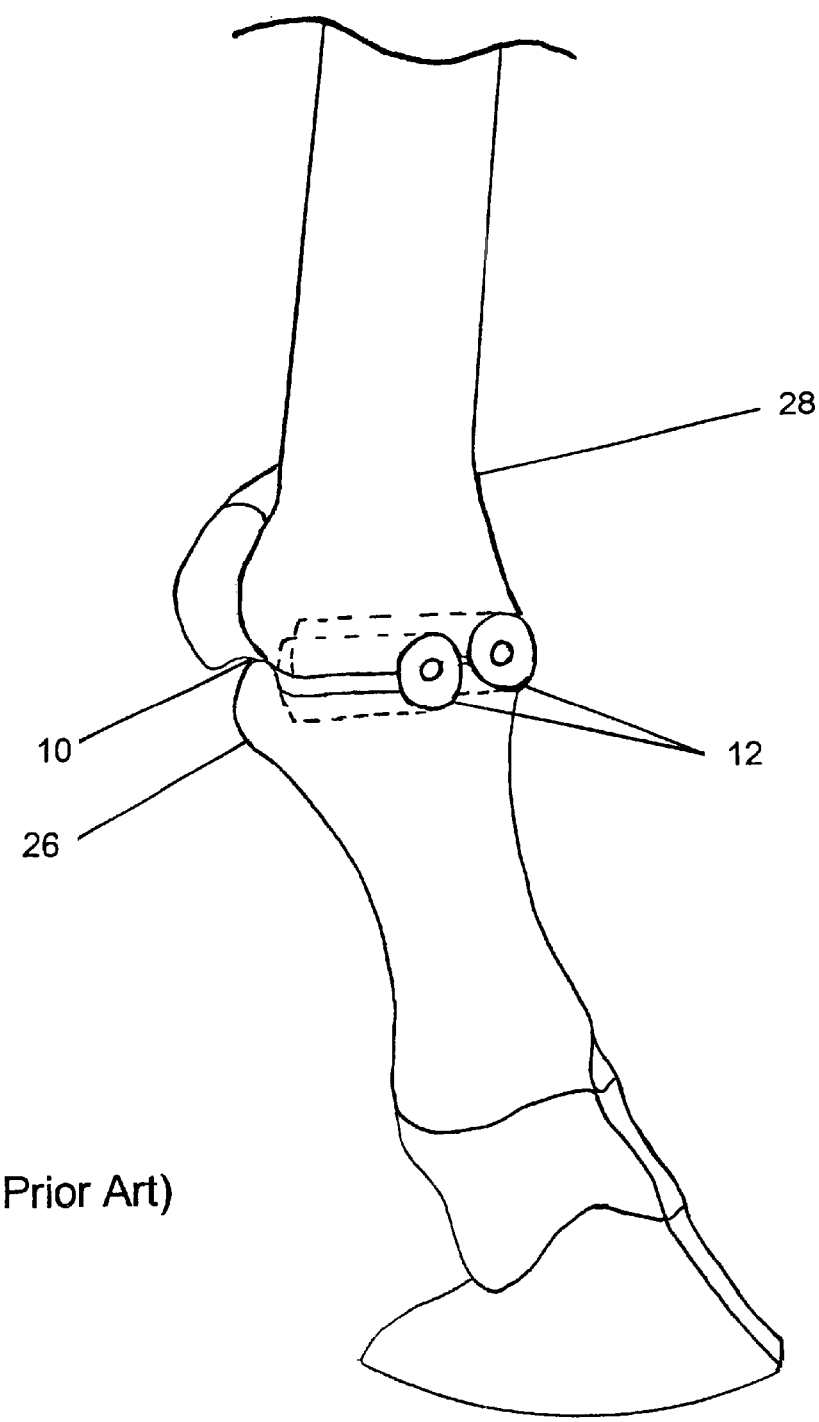
FIG. 2 illustrates a perspective view of one embodiment of a modified prior art Cloward device.
Figure 3:
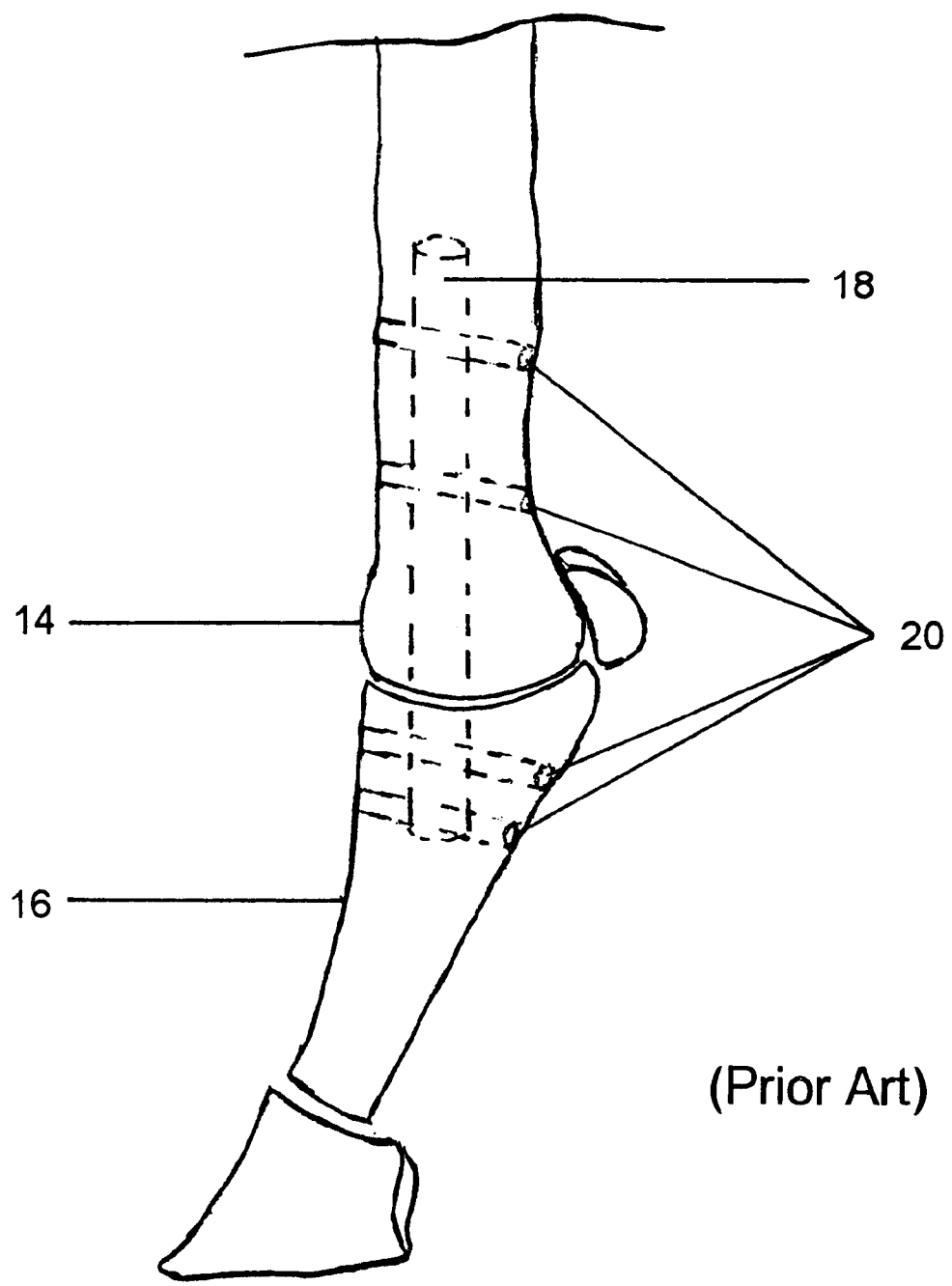
FIG. 3 illustrates a perspective view of one embodiment of a prior art interlocking intramedullary nail device.
Figure 4:
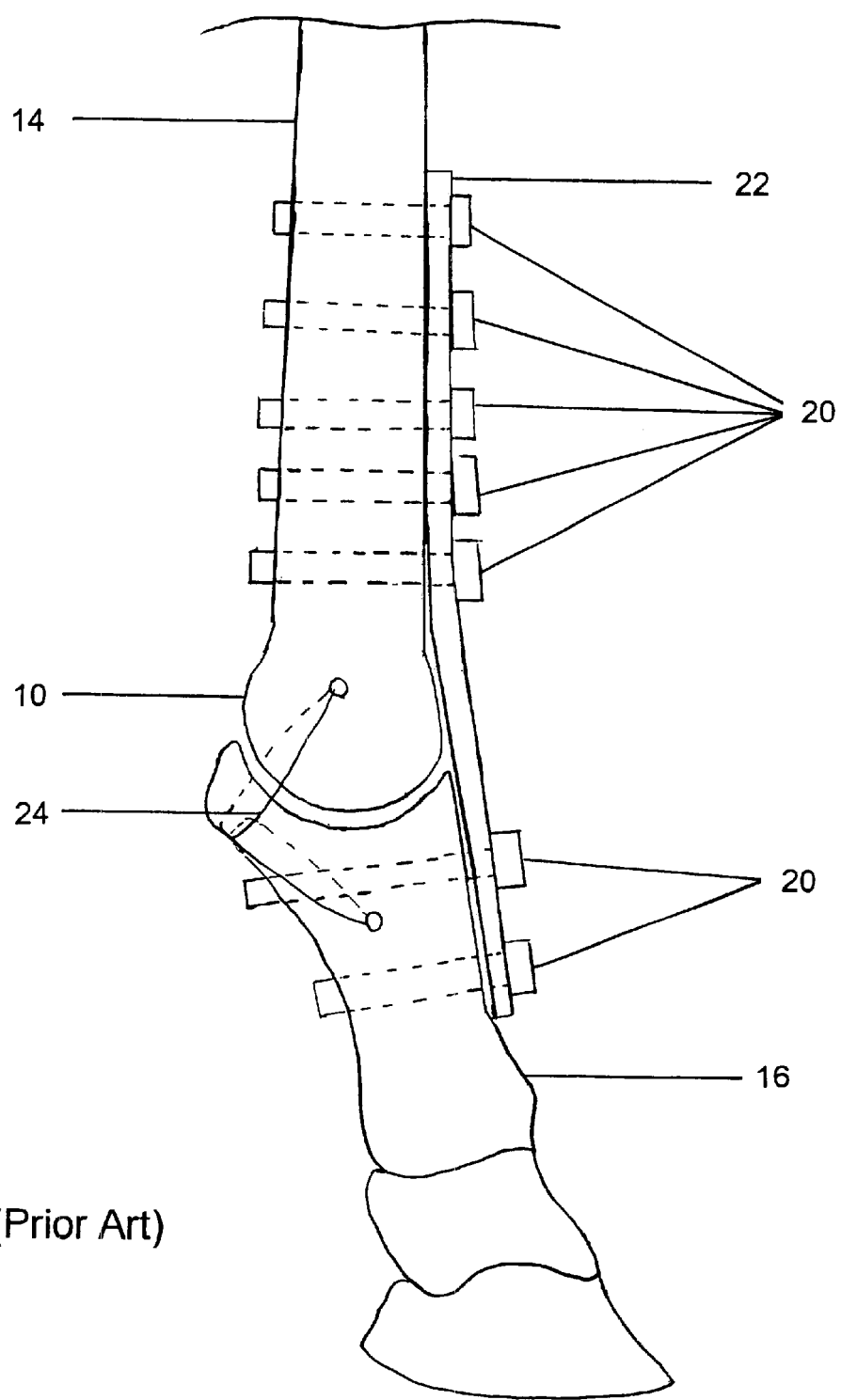
FIG. 4 illustrates a side plan view of one embodiment of a prior art plate and tension-band wire device.
Figure 5:
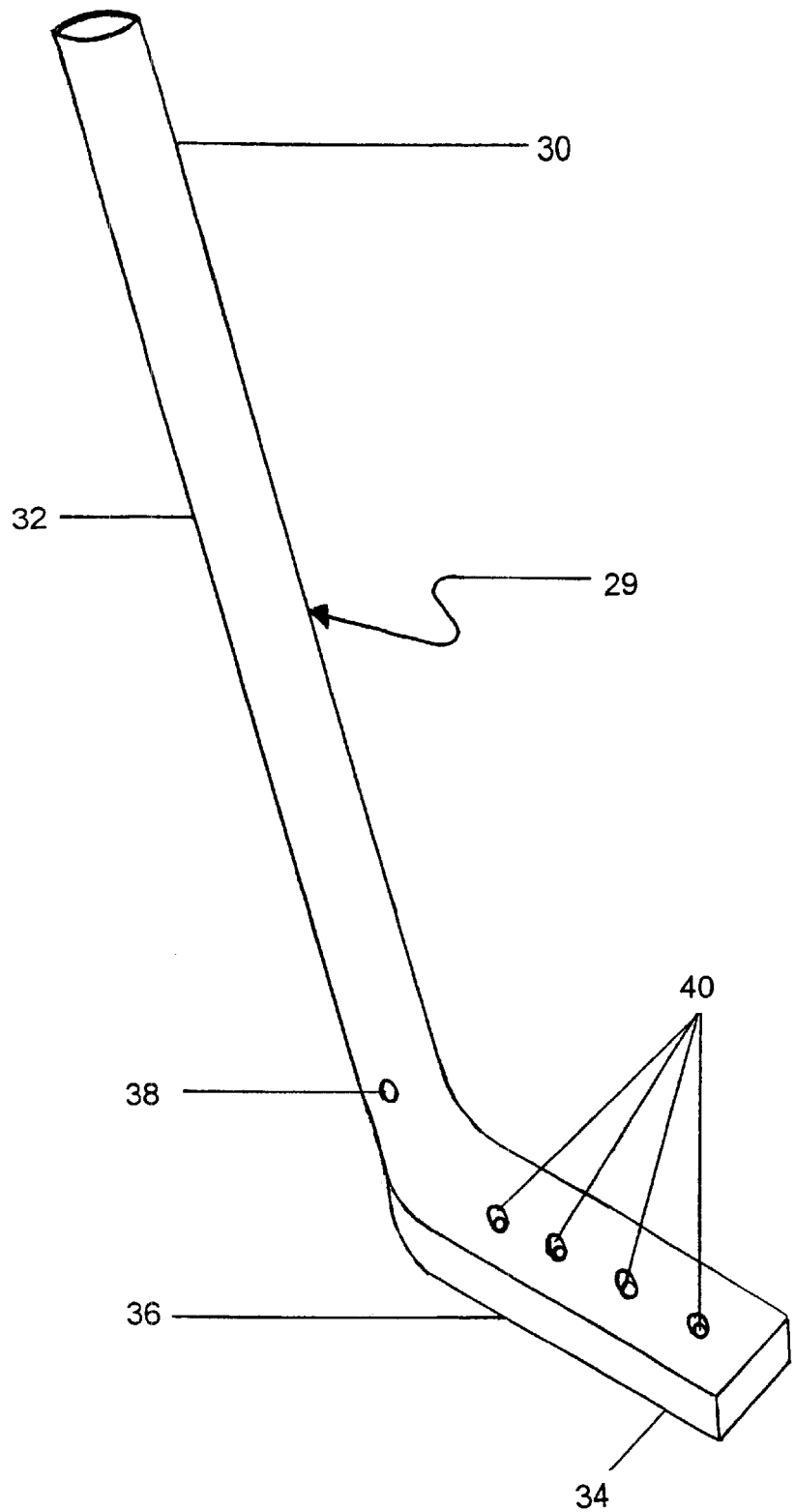
FIG. 5 illustrates a perspective view of one embodiment of the novel bone pin-plate.
Figure 6:
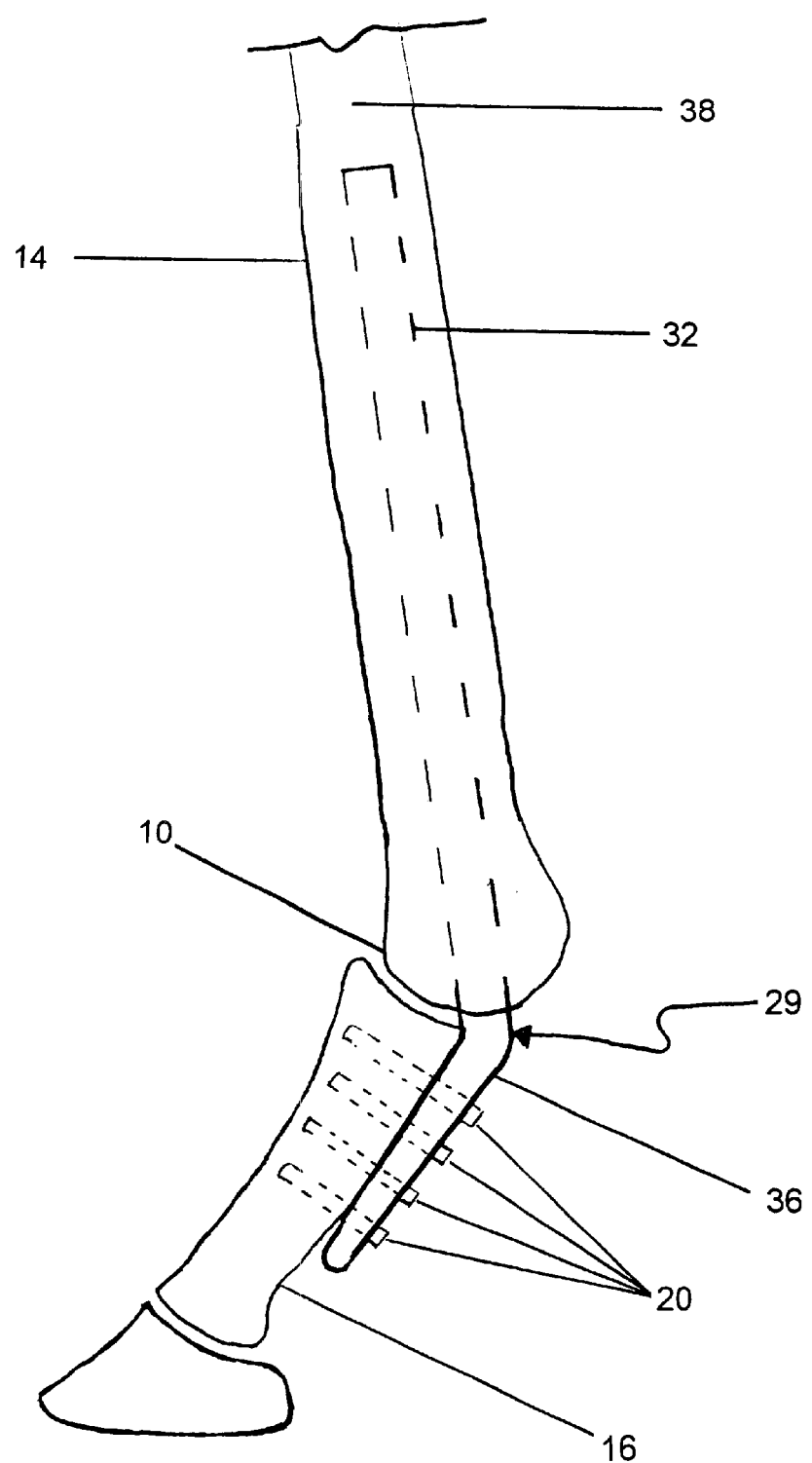
FIG. 6 illustrates a side plan view of one embodiment of the novel bone pin-plate implanted in the medullary canal of the third metacarpal bone and attached to the first phalanx.

A preferred method of surgically implanting the bone pin-plate at the fetlock joint is to use a novel palmar approach. The skin is incised along the axial mid-line from the heel bulbs to the proximal third of the third metacarpal bone. The incision is continued into the superficial digital flexor tendon ("SDFT"), transecting the SDFT sagittally into medial and lateral halves. The SDFT is then separated and retracted to expose the deep digital flexor tendon ("DDFT"). Once exposed, the DDFT is split sagittally from the middle third of the third metacarpus distally to the level of the pastern joint.

Upon splitting the DDFT, all free bony fragments are removed. The distal sesamoid bone fragments are dissected from their attachment to the distal sesamoidean ligaments. The proximal sesamoid bone fragments are then dissected from their attachments to the suspensory ligament. To avoid damaging the digital arteries, the dissection plane should be kept directly on the abaxial surface of the sesamoid bone.

Once the proximal sesamoid bone fragment has been dissected, the straight distal sesamoidean ligament is incised sagittally from its proximal limit distally to the pastern joint. The straight distal sesamoidean ligament attachments are then undermined abaxially to prepare a surface for plate application. The DDFT halves are then retracted abaxially and the fetlock joint is subluxated in extension, providing the surgeon with access to the medullary canal of the third metacarpal bone.

Upon retracting the DDFT halves, the medullary canal 38 is reamed out with a sterilized, 1.27 cm drill bit to a depth that compliments the cylindrically-shaped pin 32. The cylindrically-shaped pin 32 is inserted into the medullary canal 38 to a position below carpometacarpal joint. Once the cylindrically-shaped pin 32 has been inserted, the DDFT halves and the SDFT halves are sutured in two layers using a synthetic absorbable suture material, such as VICRYL® (Ethicon, Inc., Cincinnati, Ohio). The first layer is sutured on the deep surface of each tendon and the second layer is sutured on the superficial side of each tendon. The skin is then sutured with a non-absorbable suture, such as ETHILON® (Ethicon, Inc., Cincinnati, Ohio).

EXAMPLE 1

Construction of the Prototype

A prototype bone pin-plate 29 was constructed out of steel. The rectangular-shaped plate 36 was extended at an angle of approximately 135° from the longitudinal axis of the cylindrically-shaped pin 32. The rectangular-shaped plate 36 had a length of 7 cm, a width of 8 mm, and a thickness of 4 mm. The cylindrically-shaped pin 32 had a length of 23 cm and a diameter of 1.27 cm.

Tests Conducted

Experiments were conducted on cadavers using a prototype bone pin-plate 29. A 1.27 cm diameter hole was drilled into the medullary canal 38 for a distance of approximately 24 cm. After inserting the cylindrically-shaped pin 32 into the medullary canal 38, the fetlock joint 10 was affixed to the rectangular-shaped plate 36 in a natural position by inserting 4.5 mm diameter cortical bone screws 20 (Synthes Ltd., Paoli, Pa.) through the rectangular-shaped plate 36, and into the first phalanx 16. The bone pin-plate 29 was mounted in a support position and a load force was then applied along the longitudinal axis of the bone pin-plate 29. The bone pin-plate 29 had a yield strength of approximately 246.93 kN (55.56 kips). The moment about the fetlock joint 10 was calculated at the yield point using the dimensions of the bone pin-plate 29. The bone pin-plate 29 experienced a moment of 11.264 kN-m (99.7 kip-in) at its yield point.

Experiments were also conducted on cadavers using a plate and tension-band wire device. It was determined that a dorsally applied 12 hole bone plate and tension-band wire device had a yield point of 50 kN when loaded in compression along its longitudinal axis. Further experiments were conducted comparing a plate and tension-band wire device and a bone pin-plate device 29 on paired cadaver specimens. The dorsally applied plate and tension-band wire device was stabilized at a 10° angle of extension, while the bone pin-plate device 29 was stabilized at a 50° angle of extension.

It is known that a 450 kg horse loads each limb with an approximate force of 7.5 kN at a rate of about 125 times per hour while walking. See Les, C.M. et al., "Ex Vivo Simulation of In Vivo strain Distributions in the Equine Metacarpus," *Equine Vet J*, vol. 30, pp. 260–266 (1998); and L. McDuffee, et al., "Limb Loading Activity of Adult Horses Confined to Box Stalls in an Equine Hospital Barn," *American Journal of Veterinary Research*, vol. 61, pp. 234–237 (2000). Therefore, the plate and tension-band wire device had a yield point 6.7 times the load during a walk, while the bone pin-plate 29 had a yield point 33 times greater than the load applied while walking.

Conclusion

The bone pin-plate device had a yield point 5.2 times greater than the plate and tension-band wire device. At yield point, the plate and tension-band wire device experienced a moment of 6.9 kip-in, while the palmar bone pin-plate device 29 experienced a moment of 99.7 kip-in due, in part, to the angle of extension differences. The bone pin-plate 29 applied to the tension band surface will be much more resistant to fatigue failure.

Clinical trials will begin upon approval by the Institutional Animal Care and Use Committee. The trials will use two and three year-old Thoroughbred horses who have incurred a suspensory apparatus breakdown injury while racing at one of the race tracks in Louisiana. The clinical trials will use previously published results (e.g., Bramlage, 1985) for positive treated controls.

The complete disclosures of all references cited in this specification are hereby incorporated by reference. In the event of an otherwise irreconcilable conflict, however, the present specification shall control.

I claim:

1. A bone pin-plate for stabilizing an injured equine fetlock joint, said bone pin-plate comprising:
   (a) a proximal end comprising a rigid, cylindrical pin having a longitudinal axis, and having a size and shape adapted for insertion into the medullary canal of the equine third metacarpal bone to a position below the carpometacarpal joint, and adapted to support the weight applied to the equine fetlock joint;
   (b) a distal end having a rigid, approximately rectangular plate extending at an angle between about 105° and about 175°, from the longitudinal axis of said cylindrical pin; wherein said rectangular plate is adapted to be affixed to an equine fetlock joint in a natural position by attaching said rectangular plate to the tension side of the first phalanx; and wherein the dimensions and shape of the surface of said rectangular plate are adapted to conform to the surface of the first phalanx that is contacted by said rectangular plate.

2. A bone pin-plate device as in claim 1, wherein said rectangular plate comprises at least four drill holes adapted to receive screws to secure said plate to the first phalanx of an equine fetlock joint.

3. A bone pin-plate device as in claim 1, wherein said cylindrical pin comprises at least one hole drilled through said pin near the distal end of said pin adapted to receive a screw to secure said pin to an equine third metacarpal bone to reduce torsional movement of said pin in the third metacarpal bone.

4. A bone pin-plate device as in claim 1, wherein said rigid plate extends at an angle preferably about 135° from the longitudinal axis of said cylindrical pin.

5. A method for surgically promoting arthrodesis in an equine fetlock joint using a bone pin-plate as recited in claim 1; said method comprising inserting the cylindrical pin of the bone pin-plate into the medullary canal of the third metacarpal bone of the fetlock joint; and securing the rectangular plate of the bone pin-plate to the tension side of the first phalanx of the fetlock joint; so that the third metacarpal bone and the first phalanx assume a natural and fixed position relative to one another.

6. A method as in claim 5, wherein an incision is made from the heel bulbs of the fetlock joint to the superficial digital flexor tendon of the fetlock joint to allow the inserting of the cylindrical pin.

7. A method as in claim 6, wherein the superficial digital flexor tendon of the fetlock joint is split sagittally into medial and lateral halves, thereby exposing the deep digital flexor tendon of the fetlock joint.

8. A method as in claim 7, wherein the deep digital flexor tendon of the fetlock joint is split sagittally from the middle third of the third metacarpus of the fetlock joint distally to the level of the pastern joint of the fetlock joint.

9. A method as in claim 5, additionally comprising the step of removing all free bony fragments of the fetlock joint.

10. A method as in claim 5, additionally comprising the step of dissecting the distal sesamoid bones of the fetlock joint from their attachment to the distal sesamoidean ligaments of the fetlock joint.

11. A method as in claim 10, wherein the dissection is maintained on a plane on the abaxial surface of the sesamoid bone of the fetlock joint to avoid damage to the digital arteries of the fetlock joint.

12. A method as in claim 5, additionally comprising the step of incising the straight distal sesamoidean ligament of the fetlock joint sagittally from its proximal limit distally to the pastern joint of the fetlock joint.

13. A method as in claim 5, additionally comprising the step of undermining the attachments of the straight distal sesamoidean ligament of the fetlock joint abaxially to form a surface for securing the plate.

14. A method as in claim 5, additionally comprising the step of retracting halves of the digital flexor tendon of the fetlock joint abaxially so that the fetlock joint can be subluxated in extension, allowing access to the medullary canal of the third metacarpal bone for insertion of the pin.

15. A method as in claim 5, wherein the plate is secured to the first phalanx of an equine fetlock joint with a plurality of screws.

16. A method as in claim 5, wherein the pin is secured to the third metacarpal bone with one or more screws.

17. A method as in claim 5, wherein the distal third metacarpal bone is compressed against the first phalanx with one or more screws placed abaxially of the bone pin-plate device.

* * * * *